(12) United States Patent
Herry et al.

(10) Patent No.: US 11,872,306 B2
(45) Date of Patent: Jan. 16, 2024

(54) GRANULES OF AN ACTIVE SUBSTANCE WITH DOUBLE TASTE-MASKING TECHNIQUE, METHOD FOR THE PRODUCTION THEREOF, AND ORODISPERSIBLE TABLETS CONTAINING SAME

(71) Applicant: Ethypharm, St. Cloud (FR)

(72) Inventors: Catherine Herry, Saint-Ouen du Tilleul (FR); Caroline Ailhas, Alizay (FR)

(73) Assignee: Ethypharm, St. Cloud (FR)

( * ) Notice: Subject to any disclaimer, the term of this patent is extended or adjusted under 35 U.S.C. 154(b) by 944 days.

(21) Appl. No.: 15/523,098

(22) PCT Filed: Oct. 30, 2015

(86) PCT No.: PCT/FR2015/052936
§ 371 (c)(1),
(2) Date: Aug. 30, 2017

(87) PCT Pub. No.: WO2016/066976
PCT Pub. Date: May 6, 2016

(65) Prior Publication Data
US 2019/0125663 A1 May 2, 2019

(30) Foreign Application Priority Data
Oct. 31, 2014 (FR) ...................................... 1460532

(51) Int. Cl.
*A61K 9/00* (2006.01)
*A61K 9/16* (2006.01)
*A61K 9/20* (2006.01)

(52) U.S. Cl.
CPC .......... *A61K 9/0056* (2013.01); *A61K 9/1635* (2013.01); *A61K 9/1664* (2013.01); *A61K 9/2013* (2013.01); *A61K 9/2018* (2013.01); *A61K 9/2027* (2013.01)

(58) Field of Classification Search
None
See application file for complete search history.

(56) References Cited

U.S. PATENT DOCUMENTS

| 2007/0098746 A1* | 5/2007 | Nichols ................ A61K 31/485 424/400 |
| 2010/0215740 A1* | 8/2010 | Pilgaonkar ........... A61K 9/2009 424/465 |
| 2014/0302152 A1* | 10/2014 | Da Costa Barrocas ..................... A61K 9/1623 424/490 |

FOREIGN PATENT DOCUMENTS

| EP | 1 301 176 B1 | 3/2004 |
| FR | 2 784 895 | 10/1998 |
| FR | 2784895 A1 * | 4/2000 ........... A61K 9/1617 |
| FR | 2 850 275 | 1/2003 |
| FR | 2 848 855 | 12/2012 |
| FR | 2 999 432 | 12/2012 |
| JP | 2012153665 * | 8/2012 ............... A61K 9/50 |
| WO | WO-03059349 A1 * | 7/2003 ........... A61K 9/0056 |
| WO | WO-2004066925 A2 * | 8/2004 ........... A61K 9/0056 |
| WO | 2012/080048 A1 | 6/2012 |

OTHER PUBLICATIONS

Diosna (https://servo-lift.com/granulation-equipment/high-shear-granulators/high-shear-granulator-pvac-10-60 (Year: 2019).*
JP2012-153665_machine_translation (Year: 2012).*
Geraldine (FR2784895; wherein a machine translation is provided) (Year: 1998).*
Passerini et al (Melt granulation of pharmaceutical powders: A comparison of high-shear mixer and fluidised bed processes. International Journal of Pharmaceutics 391 (2010) 177-186), (Year: 2010).*
Wikipedia (https://en.wikipedia.org/wiki/Glass_transition downloaded on Apr. 20, 2021) (Year: 2021).*

* cited by examiner

*Primary Examiner* — Jake M Vu
(74) *Attorney, Agent, or Firm* — Dinsmore & Shohl LLP (57) ABSTRACT

The present invention relates to granules of active ingredient with double taste masking, wherein the double taste masking is achieved by a hot-melt compound selected from waxes, hydrogenated vegetable oils, fatty acids, mono-, di- and triesters of fatty acids and of glycerol, triglycerides, glycerides, polyoxylglycerides, fatty alcohols, and mixtures thereof, and a thermoplastic polymer that is soluble at a pH less than or equal to 5. The invention also relates to the method for producing these granules and to orodispersible tablets containing these coated granules.

15 Claims, 2 Drawing Sheets

GRANULES OF AN ACTIVE SUBSTANCE WITH DOUBLE TASTE-MASKING TECHNIQUE, METHOD FOR THE PRODUCTION THEREOF, AND ORODISPERSIBLE TABLETS CONTAINING SAME

The present invention relates to the pharmaceutical field, and more particularly to that of galenics.

The invention relates to oral formulations, in particular orodispersible granules and tablets, of an active ingredient with a taste and/or sensation in the mouth that are particularly unpleasant, such as trazodone.

TECHNICAL FIELD

An orodispersible tablet is a solid form which disintegrates or dissolves in the mouth, only on contact with saliva, generally in less than 60 seconds.

Orodispersible tablets represent a galenical form in full expansion, which has developed a great deal over the past few years. Indeed, orodispersible tablets have many advantages and are particularly suitable for patients who have difficulties in swallowing, for example children and the elderly. However, these populations are not the only ones to have swallowing problems or dysphagia, since approximately 30% to 50% of the population is affected by this problem. Also affected are patients who have psychiatric disorders, but also those suffering from thyroid disorders, from Parkinson's disease, from immune system deficiency diseases (AIDS) and from gastrointestinal refluxes, and also patients suffering from nausea, vomiting or motion sickness. Orodispersible tablets are also suitable for individuals who do not have easy access to water, in particular during journeys. Another advantage of said tablets is that they allow practical and discreet use.

In order to allow rapid disintegration, orodispersible tablets have a porous structure and are compressed at pressures lower than conventional tablets, the drawbacks being that they can be more fragile and difficult to handle.

A large number of methods for obtaining orodispersible tablets have been developed over the past few years. However, there are still at the current time certain characteristics which limit the industrial development of orodispersible tablets, in particular their excessive friability and their taste and sensation in the mouth, which are sometimes unpleasant.

Thus, even though orodispersible tablets remain quite a widespread form liked by patients, in particular for their practical and rapid use, a study carried out by the applicant has shown that the taste of a tablet in the mouth appears to be the most important parameter for patients and, thus, the bad taste in the mouth is one of the major causes for non-adherence to medical treatments.

In point of fact, by virtue of their nature, orodispersible tablets are intended to disintegrate in the mouth, that is to say to release the active ingredient which has a very bad taste in the mouth. It is thus essential, for the tablet to be accepted by the patient, to have sufficient taste masking.

Conventionally, the taste masking is carried out by means of coating techniques using solvents or water. However, pharmaceutical regulations are increasingly demanding with regard to the absence of traces of solvents. Furthermore, when the coating is carried out in an aqueous medium, an expensive drying step is necessary. Moreover, the amounts of coating that can be used are limited in order to ensure rapid release of the active ingredient, and they are often insufficient to obtain a taste masking of quality.

In patent applications FR 2 784 895 and EP 1 301 176, the taste masking is carried out without solvent by thermal granulation. However, this technique, which is suitable for masking the taste of ibuprofen, proves to be insufficient for masking the taste of active ingredients with a much more pronounced and unpleasant taste, such as trazodone, even if the amounts of coating are considerably increased. Moreover, it has proven to be the case that the thermal granulation technique is not suitable for using binary compositions.

It is thus important to be able to provide granules of active ingredient which has a very bad taste, such as trazodone, which exhibit satisfactory taste masking, without using solvent, without an excessive amount of taste-masking agents, and which are suitable for preparing orodispersible tablets.

Thus, one of the objectives of the invention is to obtain granules that can be used for an orodispersible tablet which has a pleasant taste in the mouth with an active ingredient of which the taste is acknowledged to be particularly bad, in particular because of its great bitterness, in particular trazodone.

The present inventors have found that this is possible by virtue of a double taste masking carried out on the active ingredient with a hot-melt compound and a thermoplastic polymer.

SUMMARY OF THE INVENTION

Thus, according to a first subject, the invention relates to granules of active ingredient, which have a double taste masking achieved with a hot-melt compound selected from waxes, hydrogenated vegetable oils, fatty acids, mono-, di- and triesters of fatty acids and of glycerol, triglycerides, glycerides, polyoxylglycerides, fatty alcohols, and mixtures thereof, and a thermoplastic polymer that is soluble at a pH less than or equal to 5.

According to a second subject, the present invention relates to a specific process for preparing the granules of the invention by carrying out two successive thermal granulation steps.

According to a third subject, the present invention relates to orodispersible tablets containing the granules of the invention.

DETAILED DESCRIPTION OF THE INVENTION

According to its first subject, the invention relates to a granule of active ingredient which has a very bad taste, such as trazodone, which has a double taste masking.

In the present invention, the term "active ingredient" is intended to mean any molecule which has a therapeutic activity. The invention relates to active ingredients which have a very bad taste. The term "very bad taste" is intended to mean, without implied distinction, an unpleasant taste and/or sensation in the mouth. Such active ingredients are at least as unpleasant in the mouth as ibuprofen. The invention is particularly suitable for trazodone.

In the present invention, the term "trazodone" is intended to mean trazodone hydrochloride as such, in amorphous form, crystalline form, in base form, in the form of hydrates or of pharmaceutically acceptable salts.

The granules of active ingredient according to the invention have a double taste masking achieved with a hot-melt compound selected from waxes, hydrogenated vegetable oils, fatty acids, mono-, di- and triesters of fatty acids and of glycerol, triglycerides, glycerides, polyoxylglycerides, fatty alcohols, and mixtures thereof, and a thermoplastic polymer that is soluble at a pH less than or equal to 5.

In the granule with double taste masking, a first taste masking is achieved with a hot-melt compound selected from waxes, hydrogenated vegetable oils, fatty acids, mono-, di- and triesters of fatty acids and of glycerol, triglycerides, glycerides, polyoxylglycerides, fatty alcohols, and mixtures thereof, and the second taste masking is achieved with a thermoplastic polymer that is soluble at a pH less than or equal to 5.

According to one embodiment of the invention, the hot-melt compound is selected from the group consisting of waxes, hydrogenated vegetable oils, fatty acids, mono-, di- and triesters of fatty acids and of glycerol, triglycerides, glycerides, polyoxylglycerides, fatty alcohols, and mixtures thereof.

The first taste masking consists of a hot-melt compound, which is solid at ambient temperature and the melting point of which is between 35 and 150° C. This compound is selected from waxes, for example carnauba wax, candelilla wax, beeswax, paraffin wax; hydrogenated vegetable oils, for example hydrogenated cottonseed, castor or soybean oils; fatty acids, for example palmitic, stearic and behenic acids; mono-, di- and triesters of fatty acids and of glycerol, for example glycol distearate; triglycerides, for example tripalmitin and tristearin; glycerides, for example a mixture of mono-di-triglycerides; polyoxylglycerides, for example mixtures of esters of polyethylene glycol, of a glyceride fraction and of free polyethylene glycol; fatty alcohols, for example cetyl alcohol and cetearyl alcohol; and mixtures thereof.

This first taste masking is achieved by thermal granulation of the active ingredient, in particular of trazodone, with said hot-melt compound.

A second taste masking consisting of a thermoplastic polymer, that is soluble at gastric pH up to pH=5, is applied to the granules comprising the hot-melt compound.

Such a thermoplastic polymer, that is soluble at gastric pH up to pH=5, may be a cationic copolymer, in particular a copolymer based on alkyl methacrylate and on alkylamine methacrylate. By way of example, mention may be made of a cationic copolymer of methylaminoethyl methacrylate, butyl methacrylate and methyl methacrylate, in particular that sold by the company Evonik under the trade name Eudragit® E PO. Any other Eudragit® E from the company Evonik can be selected as constituent of the second coating. This second taste masking is achieved by thermal granulation of the granules comprising the hot-melt compound with said thermoplastic compound.

Without wishing to be bound by any theory, the inventors are of the opinion that, during the thermal granulation, the particles of active ingredient are stuck in the hot-melt compound, the latter not forming a homogeneous layer around the particles of active ingredient as in a conventional coating, and then, during the second thermal granulation, these particles which have the hot-melt compound are stuck in the thermoplastic polymer, the latter not forming a homogeneous layer around the particles that have the hot-melt compound as in a conventional coating, but, entirely unexpectedly, the double masking makes it possible to efficiently mask the very unpleasant taste of the active ingredient despite the low quantitative proportion of thermoactive compound and of hot-melt compound.

In the present invention, the efficiency of the taste masking is determined using an Astree electronic tongue of set #2 for pharmaceutical applications, composed of 7 sensory sensors (ZZ, AB, GA, BB, CA, DA, JE), by comparing the values obtained for a formulation devoid of active ingredient (placebo) with the same formulation comprising the active ingredient. The data generated are processed by multidimensional statistical analysis using the AlphaSoft software in its version V14.1. They make it possible to define, for each formulation, the coordinates of a point and thus to calculate the Euclidean distance between these points. The smaller this distance, the better the taste masking will be. A sufficient taste masking is obtained for a formulation-placebo Euclidean distance of less than 300, preferably of less than 260.

The granule according to the invention with double taste masking is free of any trace of solvent. This is because the granule according to the invention is obtained by thermal granulation. It thus consists only of the active ingredient, in particular trazodone, of the hot-melt compound selected from waxes, hydrogenated vegetable oils, fatty acids, mono-, di- and triesters of fatty acids and of glycerol, triglycerides, glycerides, polyoxylglycerides, fatty alcohols, and mixtures thereof, and of a thermoplastic polymer that is soluble at a pH less than or equal to 5.

The granule of the invention is also characterized in that the hot-melt compound and the thermoplastic polymer are each applied separately and successively by means of 2 different thermal granulations.

According to one embodiment, the granule consists, for 100 parts by weight:
  of from 50% to 95%, preferably from 60% to 90% and even more preferentially from 70% to 85% by weight of active ingredient, preferably of trazodone; and
  of from 2% to 50%, preferably from 5% to 30% and even more preferentially from 8% to 20% by weight of hot-melt component selected from waxes, hydrogenated vegetable oils, fatty acids, mono-, di- and triesters of fatty acids and of glycerol, triglycerides, glycerides, polyoxylglycerides, fatty alcohols, and mixtures thereof; and
  of from 5% to 30%, preferably from 8% to 25% and even more preferentially from 10% to 20% by weight of thermoplastic polymer which is soluble at a pH less than or equal to 5.

According to one particular embodiment, the granule according to the invention consists, for 100 parts by weight:
  of from 50% to 95%, preferably from 60% to 90% and even more preferentially from 70% to 85% by weight of active ingredient, preferably of trazodone; and
  of from 10% to 25%, preferably from 15% to 20% by weight of glyceryl distearate; and
  of from 5% to 20%, preferably from 10% to 15% by weight of cationic copolymer of dimethylaminoethyl methacrylate, butyl methacrylate and methyl methacrylate.

According to another aspect, the present invention relates to a process for producing the granules described above.

The present inventors have tried to produce granules coated by thermal granulation of a mixture of hot-melt compound and of polymer described above, but this thermal granulation has proved to be impossible (see comparative example 2).

In order to overcome this difficulty, the present inventors have developed the process according to the invention wherein two successive thermal granulation steps are carried out.

Thus, the present process for producing the granules with double taste masking comprises:
 a) a first step of thermal granulation, in the presence of the active ingredient, of a hot-melt compound selected from waxes, for example carnauba wax, candelilla wax, beeswax, paraffin wax; hydrogenated vegetable oils, for example hydrogenated cottonseed, castor or soybean oils; fatty acids, for example palmitic, stearic and behenic acids; mono-, di- and triesters of fatty acids and of glycerol, for example glycol distearate; triglycerides, for example tripalmitin and tristearin; glycerides, for example a mixture of mono-di-triglycerides; polyoxylglycerides, for example mixtures of esters of polyethylene glycol, of a glyceride fraction and of free polyethylene glycol; fatty alcohols, for example cetyl alcohol and cetearyl alcohol; and mixtures thereof, or else of a thermoplastic polymer which is soluble at a pH less than or equal to 5; and
 b) a second step of thermal granulation around the granule obtained in step a) or else a hot-melt compound selected from waxes, for example carnauba wax, candelilla wax, beeswax, paraffin wax; hydrogenated vegetable oils, for example hydrogenated cottonseed, castor or soybean oils; fatty acids, for example palmitic, stearic and behenic acids; mono-, di- and triesters of fatty acids and of glycerol, for example glycol distearate; triglycerides, for example tripalmitin and tristearin; glycerides, for example a mixture of mono-di-triglycerides; polyoxylglycerides, for example mixtures of esters of polyethylene glycol, of a glyceride fraction and of free polyethylene glycol; fatty alcohols, for example cetyl alcohol and cetearyl alcohol; and mixtures thereof, or else a thermoplastic polymer which is soluble at a pH less than or equal to 5.

According to one particular embodiment, the process comprises:
 a) a first step of thermal granulation, in the presence of the active ingredient, preferably of trazodone, of a hot-melt compound selected form waxes, for example carnauba wax, candelilla wax, beeswax, paraffin wax; hydrogenated vegetable oils, for example hydrogenated cottonseed, castor or soybean oils; fatty acids, for example palmitic, stearic and behenic acids; mono-, di- and triesters of fatty acids and of glycerol, for example glycol distearate; triglycerides, for example tripalmitin and tristearin; glycerides, for example a mixture of mono-di-triglycerides; polyoxylglycerides, for example mixtures of esters of polyethylene glycol, of a glyceride fraction and of free polyethylene glycol; fatty alcohols, for example cetyl alcohol and cetearyl alcohol; and mixtures thereof; and
 b) a second step of thermal granulation around the granule obtained in step a) of thermoplastic polymer that is soluble at a pH less than or equal to 5.

The process according to the invention is carried out in a high-shear granulator, for example of Diosna P-VAC 10 type, which comprises two successive thermal granulation steps. Each thermal granulation step is divided up into 3 phases according to the Temperature/Power couple registered:
 Mixing phase: the power registered remains stable while the temperature of the mixture gradually increases;
 Granulation phase: the temperature of the mixture remains stable while the power increases;
 Cooling phase: the temperature of the mixture and the power decrease.

The setpoint parameters of the granulator which make it possible to control the power and the temperature of the mixture during the process are: the paddle speed, the lump breaker speed and the setpoint temperature of the jacket.

In the present invention, the paddle speed and the lump breaker speed are expressed in revolutions per minute (rpm).

Thus, according to the invention, the process comprises two successive thermal granulation steps:
 the first step a) comprises:
 mixing of active ingredient, preferably of trazodone, and of the hot-melt component, at constant paddle speeds between 500 rpm and 200 rpm and constant lump breaker speeds between 1300 rpm and 800 rpm and while increasing the temperature of the material, from ambient temperature to the melting point ($M_p$) of the hot-melt component +/−10° C., preferably +/−5° C.;
 granulation at the melting point ($M_p$) of the hot-melt component +/−10° C., preferably +/−5° C. and at constant paddle speeds that are increased relative to the mixing step, between 500 rpm and 200 rpm, and constant lump breaker speeds that are increased relative to the mixing step, between 1500 rpm and 1000 rpm;
 cooling during which the temperature is decreased to ambient temperature and the paddle speeds are decreased relative to those of the granulation step, between 300 rpm and 100 rpm and the lump breaker speeds are decreased relative to those of the granulation step, between 1500 revolutions per minute and 1000 revolutions per minute;
 the second step b) of thermal granulation comprises:
 mixing the granules obtained in step a) with the polymer that is soluble at a pH less than or equal to 5;
 granulation at a temperature below the temperature used during the mixing and the granulation of step a), and equal to the glass transition temperature ($T_g$) of the thermoplastic component +/−10° C., preferably +/−5° C., and at constant paddle speeds that are decreased relative to the mixing step of step a), between 200 rpm and 100 rpm, and constant lump breaker speeds that are decreased relative to the mixing step of step a), between 1000 rpm and 800 rpm, then the granules obtained are cooled to ambient temperature with a paddle speed decreased to 100 rpm and a constant lump breaker speed identical to the mixing step of step b).

The mean dimension D[4,3], measured by dry laser diffraction (for example on a Mastersizer 2000 equipped with the Scirocco 2000 module), of the granules finally obtained is from 50 μm to 500 μm, preferably from 100 μm to 300 μm, preferably approximately 200 μm.

The present invention also relates to orodispersible tablets containing the granules according to the invention or prepared according to the invention.

For the purposes of the present invention, an orodispersible tablet is a tablet which disintegrates or dissolves in the mouth, only on contact with saliva, without the provision of water and without being chewed, in less than 60 seconds, preferably in less than 40 seconds, and even more preferentially in less than 30 seconds, while forming a suspension that is easy to swallow.

The disintegration (or disaggregation) time in the mouth corresponds to the duration which separates, on the one hand, the moment the tablet is placed in the mouth in contact with saliva and, on the other hand, the moment the suspension resulting from the disintegration (disaggregation) of the tablet in contact with saliva is swallowed. This disintegration time corresponds to the in vivo disintegration time.

The in vitro disintegration time of the orodispersible tablets according to the invention can also be measured. This disintegration time is measured according to the European Pharmacopeia 2.9.1 on an Erweka ZT 31 instrument or any other instrument for measuring the disintegration time of tablets corresponding to European Pharmacopeia 2.9.1. The in vitro disintegration time of the tablets according to the invention is from 10 to 30 seconds.

The orodispersible tablet of the invention comprises coated granules of active ingredient, as defined above, and a mixture of compression excipients selected from the group comprising a diluent, a disintegrant, a sweetener, a humectant, a lubricant, a flavoring agent, a dye and mixtures thereof. It can also contain a binder and/or a wetting agent.

The diluent is selected from the group comprising mannitol, xylitol, sorbitol, maltitol and mixtures thereof.

The disintegrant is selected from the group comprising crospovidone, sodium croscarmellose (AcDiSol®), sodium carboxymethyl starch (Explotab®) and mixtures thereof.

The sweetener is selected from the group comprising aspartame, potassium acesulfame, sodium saccharinate, sucralose and mixtures thereof.

The humectant is selected from the group comprising silica, preferably that sold under the name Syloid® 244 FP, hydrophobic colloidal silica, preferably that sold under the name Aerosil® R 972, precipitated silica, preferably that sold under the name Aerosil® 200, and mixtures thereof.

The lubricant is selected from the group of hydrophobic lubricants, such as magnesium stearate, or hydrophilic lubricants selected from the group comprising sodium stearyl fumarate and sodium lauryl sulfate.

The flavoring agent and the dye that can go to make up the orodispersible tablets are selected from those which are pharmaceutically acceptable. They are selected according to the organoleptic characteristics desired for the orodispersible tablet, in particular according to the category of patients for whom they are intended. Examples of flavoring agents are banana flavoring, tutti-frutti flavoring, mint flavoring, strawberry flavoring, cranberry flavoring, blackcurrant flavoring, caramel flavoring, coca flavoring, chocolate flavoring. Flavorings that are particularly suitable are strawberry flavoring and chocolate flavoring.

The binder, when it is present, is selected from the group comprising hydroxypropylmethylcellulose, polyvinylpyrrolidone, hydroxypropylcellulose with a low degree of substitution, gum arabic, cornstarch, pregelatinized starch, maltodextrins and mixtures thereof.

The wetting agent, when it is present, is selected from the group comprising poloxamers, macrogols, macrogolglycerides, and polysorbates, said wetting agent preferably being the macrogolglycerides sold under the name Gelucire® 44/14.

The orodispersible tablets according to the invention can be produced by direct compression, that is to say by dry compression of the coated granules of active ingredient and of the compression excipients which are optionally pregranulated. According to another embodiment, the orodispersible tablets according to the invention can be produced by compression-molding, as described in patent application FR 2 999 432 in the name of the applicant, in which case it is possible for the mixture of excipients to also comprise a wetting agent and/or a binder.

According to one particular embodiment, the compression excipients are in the form of grains of excipients.

The grains of excipients have a median particle size of between +30% and −30%, preferably between +10% and −10%, relative to the size of the coated granules of active ingredient. Thus, the size of the grains of excipients is from 70 μm to 650 μm, preferably from 180 μm to 440 μm.

According to one embodiment of the invention, the mixture of excipients, optionally in the form of grains, comprises:
from 65% to 90%, and preferably from 70% to 80%, of a diluent, preferably the mannitol sold under the name Mannitol 200,
from 2% to 25%, and preferably from 10% to 20%, of a disintegrant, preferably the crospovidone sold under the name Polyplasdone® XL,
from 1% to 8%, and preferably from 3% to 5%, of a sweetener, preferably sucralose,
from 0% to 5%, and preferably from 0.5% to 3%, of a humectant,
from 0% to 5% of a lubricant,
from 0% to 8%, and preferably from 0.5% to 4%, of a flavoring agent and/or of a dye,
the percentages being percentages by weight relative to the total weight of the tablets.

According to another embodiment of the invention, the tablet is produced by applying compression forces ranging from 1 to 20 Kn (kNewtons), and preferably from 2 to 6 kN.

By way of example, the orodispersible tablet of the invention has:
a weight ranging from 100 to 600 mg, and preferably from 200 to 400 mg,
a thickness ranging from 1 to 8 mm, and preferably from 4 to 6 mm,
a diameter of from 7 to 14 mm, and preferably from 8 to 12 mm.

Thus, such tablets can easily be placed in the oral cavity, on the tongue where they disintegrate owing to the presence of saliva and the natural pressure exerted between the tongue and the palate when the mouth is closed again.

According to another embodiment, the tablets can comprise at least one notch which enables them to break in order to administer a smaller amount of active ingredient.

The orodispersible tablet according to the invention has a hardness ranging from 20 to 80 N, and preferably from 30 to 65 N. The method for measuring the hardness is that of European Pharmacopeia 2.9.8.

By way of indication, the orodispersible tablet of the invention has a friability ranging from 0.0% to 0.6%, and preferably from 0.1% to 0.4%. The friability is measured on an Erweka TA 10 instrument according to the method described in the European Pharmacopeia (edition 7, chapter 2.9.7.) Because of this satisfactory friability, it is possible to use conventional industrial methods for transferring and packaging the tablets which do not require particular precautions and which enable very fast execution.

The invention will be understood more clearly in the light of the nonlimiting and purely illustrative examples which follow and the figures.

EXAMPLES

In what follows, the following commercial products are used:
Precirol® ATO 5: glyceryl distearate, sold by Gattefossé;
Dynasan® 114: trimyristin, ester of glycerine substituted with C14 fatty acids, sold by Cremer Oleo Division;

Softisan® 154: derived from hydrogenated palm oil, mixture of triglycerides (palmitic and stearic) and of fatty acids having a chain length ranging from C10 to C18, sold by Cremer Oleo Division;

Lipoxol® 3 350: polyethylene glycols, known under trade names such as Macrogols, PEG or else Carbowax, sold by Sasol;

Compritol® HD5 ATO: behenoyl polyoxyl-8 glycerides, mixture of PEG and of mono-, di- and triglycerides, sold by Gattefossé;

Montane® 60 PHA: sorbitan stearate, derived from sorbitol and stearic acid, sold by SEPPIC;

Crodacol® CS 50: cetostearyl alcohol, mixture of chains comprising 16 carbon atoms and chains comprising 18 carbon atoms, sold by Croda Inc;

Crodacol® S 95: stearyl alcohol, fatty alcohol with a chain length of 18 carbon atoms, sold by Croda Inc;

Crodacol® C 95: cetyl alcohol, fatty alcohol with a chain length of 16 carbon atoms, sold by Croda Inc;

Bitrex: denatonium benzoate, the most bitter substance discovered to date, used as bittering agent in order to simulate the bitterness of an active ingredient;

Eudragit® E PO: cationic copolymer based on dimethylaminoethyl methacrylate, butyl methacrylate and methyl methacrylate—(CAS number 24938-16-7) sold by Evonik;

AcDiSol®: sodium croscarmellose, sold by FMC Biopolymer;

Polyplasdone XL: crospovidone, sold by ISP Pharmaceutical;

Mannitol SD 200: mannitol, sold by Roquette;

Syloid® 244FP: silica, sold by Grace Davison.

Example 1

Step 1: Thermal Granulation Using Precirol ATO 5

The active ingredient and the Precirol ATO 5 are introduced into a high-shear granulator of Diosna P-VAC10 type in the proportions indicated in table 1. Depending on the density of the mixture, the total weight introduced is adjusted by those skilled in the art to the filling volume of the tank of the granulator so as to guarantee homogenization thereof throughout the thermal granulation process (ideally ⅔ of the volume).

By way of information, the percentages given in the present invention are a weight-to-weight ratio (w/w).

TABLE 1

| Centesimal formula of the grain | | |
|---|---|---|
| Ingredients | | % (w/w) |
| Trazodone HCl | Active ingredient | 80.00 |
| Precirol ATO 5 | Hot-melt binder | 20.00 |
| Total | | 100.00 |

According to example 1, the setpoint parameters used, namely: paddle speed, lump breaker speed and jacket setpoint temperature, are indicated in table 2.

TABLE 2

| Mixing | | | Granulation | | | Cooling | | |
|---|---|---|---|---|---|---|---|---|
| Paddle speed (rpm) | Lump breaker speed (rpm) | Jacket T (° C.) | Paddle speed (rpm) | Lump breaker speed (rpm) | Jacket T (° C.) | Paddle speed (rpm) | Lump breaker speed (rpm) | Jacket T (° C.) |
| 500 | 1000 | 65 | 400 | 1500 | 57 | 200 to 100 | 1000 | 10 |

Once it has returned to ambient temperature, the grain obtained is discharged and calibrated by means of an Erweka AR402 drive unit equipped with an FGS-type oscillating calibrator on a 500 μm grille, at a speed of 10 cpm.

Step 2: Thermal Granulation by Means of Precirol ATO 5 and Eudragit E PO

The grain obtained according to step 1 above is introduced into a high-shear granulator of Diosna P-VAC10 type in the proportions indicated in table 3. Depending on the density of the mixture, the total mass introduced is adjusted to the filling volume of the tank of the granulator so as to guarantee homogenization thereof throughout the thermal granulation process (ideally ⅔ of the volume).

TABLE 3

| Centesimal formula of the grain | | | |
|---|---|---|---|
| | Ingredients | | % (w/w) |
| Grain Example 1 | Trazodone HCl Precirol ATO 5 | Active ingredient Hot-melt binder | 72.00 18.00 |
| Eudragit E PO | | Thermoplastic polymer | 10.00 |
| Total | | | 100.0 |

The setpoint parameters used are indicated in Table 4.

TABLE 4

| Mixing | | | Granulation | | | Cooling | | |
|---|---|---|---|---|---|---|---|---|
| Paddle speed (rpm) | Lump breaker speed (rpm) | Jacket T (° C.) | Paddle speed (rpm) | Lump breaker speed (rpm) | Jacket T (° C.) | Paddle speed (rpm) | Lump breaker speed (rpm) | Jacket T (° C.) |
| 250 | 1000 | 48 | 250 | 1000 | 52 | 200 to 100 | 1000 | 10 |

Once it has returned to ambient temperature, the grain obtained is discharged and calibrated by means of an Erweka R402 drive unit equipped with an FGS-type oscillating calibrator on a 500 µm grille, at a speed of 10 cpm.

Example 2 (Comparative)

Thermal Granulation by Means of a Precirol ATO 5/Eudragit E PO Mixture

The active ingredient, the Precirol ATO 5 and the Eudragit E PO are introduced into a high-shear granulator of Diosna P-VAC10 type in the proportions indicated in table 5. Depending on the density of the mixture, the total weight introduced is adjusted by those skilled in the art to the filling volume of the tank of the granulator so as to guarantee homogenization thereof throughout the thermal granulation process (ideally ⅔ of the volume).

TABLE 5

| Centesimal formula of the grain | | |
|---|---|---|
| Ingredients | | % (w/w) |
| Trazodone HCl | Active ingredient | 72.00 |
| Precirol ATO 5 | Hot-melt binder | 18.00 |
| Eudragit E PO | Thermoplastic polymer | 10.00 |
| Total | | 100.0 |

According to example 2, the setpoint parameters used are indicated in table 6.

TABLE 6

| Mixing | | | Granulation | | | Cooling | | |
|---|---|---|---|---|---|---|---|---|
| Paddle speed (rpm) | Lump breaker speed (rpm) | Jacket T (° C.) | Paddle speed (rpm) | Lump breaker speed (rpm) | Jacket T (° C.) | Paddle speed (rpm) | Lump breaker speed (rpm) | Jacket T (° C.) |
| 300 | 1000 | 65 | 300 | 1500 | 60 | 300-100 | 1000 | 10 |

The thermal granulation by means of a mixture of Precirol ATO 5 and Eudragit E PO is not technically controllable: an overgranulation at the granulation step causes a major overgranulation at cooling. The grain obtained is then in the form of a hard paste which can lead to the high-shear granulator being damaged and can make it impossible to calibrate it in yields compatible with an industrial process.

Example 3

Compression of the Grain of Step 1 of Example 1, 30 mg Dosage

The grain produced at the end of step 1 of example 1 is used in the production of tablets containing a dose of 30 mg of trazodone hydrochloride. The mixing and then the lubrication are carried out according to the proportions indicated in table 7 by means of a cubic mixer equipped with a tank of suitable size or any other item of equipment ensuring good mixture homogeneity.

TABLE 7

| Orodispersible tablet centesimal composition | | | | Dosage 30 mg |
|---|---|---|---|---|
| Ingredients | | | % (w/w) | mg/tablet |
| Grain | Trazodone HCl API | Active ingredient | 15.00 | 30.00 |
| Example 1 | Precirol ATO 5 | Hot-melt binder | 3.75 | 7.50 |
| AcDisol | | Disintegrant | 5.00 | 10.00 |
| Polyplasdone XL | | Disintegrant | 2.00 | 4.00 |
| Mannitol SD 200 | | Diluent | 68.45 | 136.90 |
| Flavoring | | Flavoring | 1.00 | 2.00 |
| Sucralose | | Sweetener | 1.00 | 2.00 |
| Dye | | Dye | 1.00 | 2.00 |
| Syloid 244FP | | Humectant | 2.00 | 4.00 |
| Mg stearate | | Lubricant | 0.80 | 1.60 |
| Total | | | 100.0 | 200.0 |

The mixture is compressed on a Fette 102i rotary press equipped with a gravity distributor and 3 sets of matrix/round punches, diameter 8 mm, and a splitting bar. The target unit weight is 200 mg and the compression force is adjusted to obtain a target hardness of 60 N.

Example 4

Compression of the Grain of Example 1, 30 mg Dosage

The grain produced according to example 1 is used in the production of orodispersible tablets containing a 30 mg dose of trazodone hydrochloride. The mixing and then the lubrication are carried out according to the proportions indicated in table 8 by means of a cubic mixer equipped with a tank of suitable size or any other item of equipment ensuring good mixture homogeneity.

TABLE 8

| Orodispersible tablet centesimal composition | | | % (w/w) | mg/ tablet |
|---|---|---|---|---|
| | Ingredients | | | |
| Grain step 2 | Trazodone HCl API | Active ingredient | 15.00 | 30.00 |
| | Precirol ATO 5 | Hot-melt binder | 3.75 | 7.50 |
| | Eudragit E PO | Thermoplastic polymer | 2.08 | 4.17 |
| AcDisol | | Disintegrant | 5.00 | 10.00 |
| Polyplasdone XL | | Disintegrant | 2.00 | 4.00 |
| Mannitol SD 200 | | Diluent | 66.37 | 132.73 |
| Flavoring | | Flavoring | 1.00 | 2.00 |
| Sucralose | | Sweetener | 1.00 | 2.00 |
| Dye | | Dye | 1.00 | 2.00 |
| Syloid 244FP | | Humectant | 2.00 | 4.00 |
| Mg stearate | | Lubricant | 0.80 | 1.60 |
| Total | | | 100.0 | 200.0 |

The mixture is compressed on a Fette 102i rotary press equipped with a gravity distributor and 3 sets of matrix/round punches, diameter 8 mm, and 1 splitting bar. The target unit weight is 200 mg and the compression force is adjusted so as to obtain a target hardness of 35N.

According to example 4, the flavoring used can be a strawberry or chocolate flavoring (flavorings supplied by Firmenich, pharmaceutical grade).

Example 5

Compression of the Grain of Example 1, 90 mg Dosage

The grain produced according to example 1 is used in the production of orodispersible tablets, containing a 90 mg dose of trazodone hydrochloride. The mixing and then the lubrication are carried out according to the proportions indicated in Table 9 by means of a cubic mixer equipped with a tank of suitable size or any other item of equipment ensuring good mixture homogeneity.

TABLE 9

| Centesimal formula | | | | Dosage 90 mg |
|---|---|---|---|---|
| | Ingredients | | % (w/w) | mg/ tablet |
| Grain Example 3 | Trazodone HCl API | Active ingredient | 22.50 | 90.00 |
| | Precirol ATO 5 | Hot-melt binder | 5.63 | 22.50 |
| | Eudragit E PO | Thermoplastic polymer | 3.13 | 12.50 |

TABLE 9-continued

| Centesimal formula | | | Dosage 90 mg |
|---|---|---|---|
| Ingredients | | % (w/w) | mg/ tablet |
| AcDisol | Disintegrant | 5.00 | 20.00 |
| Polyplasdone XL | Disintegrant | 2.00 | 8.00 |
| Mannitol SD 200 | Diluent | 55.95 | 223.80 |
| Flavoring | Flavoring | 1.00 | 4.00 |
| Sucralose | Sweetener | 1.00 | 4.00 |
| Dye | Dye | 1.00 | 4.00 |
| Syloid 244FP | Humectant | 2.00 | 8.00 |
| Mg stearate | Lubricant | 0.80 | 3.20 |
| Total | | 100.0 | 400.0 |

The mixture is compressed on a Fette 102i rotary press equipped with a gravity distributor and 3 sets of matrix/round punches, diameter 11 mm. The target unit weight is 400 mg and the compression force is adjusted so as to obtain a target hardness of 30 N.

Example 6

Step 1: Thermal Granulation by Means of Dynasan 114+ Trazodone

The active ingredient and the Dynasan 114 are introduced into a high-shear granulator of Diosna P-VAC10 type in the proportions indicated in table 10. Depending on the density of the mixture, the total weight introduced is adjusted by those skilled in the art to the filling volume of the tank of the granulator so as to guarantee homogenization thereof throughout the thermal granulation process (ideally ⅔ of the volume).

TABLE 10

| Centesimal formula of the grain | | | |
|---|---|---|---|
| Ingredients | | % (w/w) | Weight (grams) |
| Trazodone HCl | Active ingredient | 77.05 | 402.9 |
| Dynasan 114 | Hot-melt binder | 22.9 | 120.0 |
| Total | | 100.0 | 522.9 |

The setpoint parameters used, namely: the paddle speed, the lump breaker speed and the setpoint temperature of the jacket, are indicated in table 11.

TABLE 11

| Mixing | | | Granulation | | | Cooling | | |
|---|---|---|---|---|---|---|---|---|
| Paddle speed (rpm) | Lump breaker speed (rpm) | Jacket T (° C.) | Paddle speed (rpm) | Lump breaker speed (rpm) | Jacket T (° C.) | Paddle speed (rpm) | Lump breaker speed (rpm) | Jacket T (° C.) |
| 300 | 1000 | 70 | 300 | 1500 | 65 | 100 | 1000 | 10 |

Once it has returned to ambient temperature, the grain obtained is discharged and calibrated by means of an Erweka AR402 drive unit equipped with an FGS-type oscillating calibrator on a 500 μm grille, at a speed of 10 cpm.

Step 2: Thermal Granulation by Means of Dynasan 114 and Eudragit E PO

The grain obtained in step 1 is introduced into a high-shear granulator of Diosna P-VAC10 type in the proportions indicated in table 12. Depending on the density of the mixture, the total weight introduced is adjusted to the filling volume of the tank of the granulator so as to guarantee homogenization thereof throughout the thermal granulation process (ideally ⅔ of the volume).

TABLE 12

Centesimal formula of the grain

| Ingredients | | | % (w/w) |
|---|---|---|---|
| Grain Example 7 | Trazodone HCl Dyanasan 114 | Active ingredient Hot-melt binder | 90.00 |
| Eudragit E PO | | Thermoplastic polymer | 10.00 |
| Total | | | 100.0 |

The setpoint parameters used are indicated in table 13.

TABLE 13

| Mixing | | | Cooling | | |
|---|---|---|---|---|---|
| Paddle speed (rpm) | Lump breaker speed (rpm) | Jacket T (° C.) | Paddle speed (rpm) | Lump breaker speed (rpm) | Jacket T (° C.) |
| 300 | 800 | 53 | 100 | 800 | 10 |

Once it has returned to ambient temperature, the grain obtained is discharged and calibrated by means of an Erweka AR402 drive unit equipped with an FGS-type oscillating calibrator on a 500 μm grid, at a speed of 10 cpm.

Example 7

Compression of the Grain of Example 6, 60 mg Dosage

The grain produced according to example 6 is used in the production of tablets containing a 60 mg dose of trazodone hydrochloride. The mixing and then the lubrication are carried out according to the proportions indicated in table 14 by means of a cubic mixer equipped with a tank of suitable size or any other item of equipment ensuring good mixture homogeneity.

TABLE 14

| Orodispersible tablet centesimal composition | | | % (w/w) | Dosage 60 mg mg/ tablet |
|---|---|---|---|---|
| Grain Example 8 | Trazodone HCl Dynasan 114 Eudragit E PO | Active ingredient Hot-melt binder Thermoplastic polymer | 20.00 5.00 2.94 | 60.00 15.00 8.83 |
| AcDisol | | Disintegrant | 2.00 | 6.00 |
| Crospovidone XL | | Disintegrant | 5.00 | 15.00 |
| Mannitol SD 200 | | Diluent | 60.26 | 180.77 |
| Flavoring | | Flavoring | 1.00 | 3.00 |
| Sucralose | | Sweetener | 1.00 | 3.00 |
| Syloid 244FP | | Humectant | 2.00 | 6.00 |
| Mg stearate | | Lubricant | 0.80 | 2.40 |
| Total | | | 100.0 | 300.0 |

The mixture is compressed on a Fette 102i rotary press equipped with a gravity distributor and 3 sets of matrix/convex round punches, diameter 10 mm, and a splitting bar. The target unit weight is 300 mg and the compression force is adjusted so as to obtain a target hardness of 22 N.

Example 8

Step 1: Thermal Granulation by Means of Softisan 154+ Trazodone

The active ingredient and the Softisan 154 are introduced into a high-shear granulator of Diosna P-VAC10 type in the proportions indicated in table 15. Depending on the density of the mixture, the total weight introduced is adjusted by those skilled in the art to the filling volume of the tank of the granulator so as to guarantee homogenization thereof throughout the thermal granulation process (ideally ⅔ of the volume).

TABLE 15

Centesimal formula of the grain

| Ingredients | | % (w/w) | Weight (grams) |
|---|---|---|---|
| Trazodone HCl | Active ingredient | 80 | 480.00 |
| Softisan 154 | Hot-melt binder | 20 | 120.00 |
| Total | | 100.0 | 600.00 |

The setpoint parameters used, namely: the paddle speed, the lump breaker speed and the setpoint temperature of the jacket, are indicated in table 16.

TABLE 16

| Mixing | | | Granulation | | | Cooling | | |
|---|---|---|---|---|---|---|---|---|
| Paddle speed (rpm) | Lump breaker speed (rpm) | Jacket T (° C.) | Paddle speed (rpm) | Lump breaker speed (rpm) | Jacket T (° C.) | Paddle speed (rpm) | Lump breaker speed (rpm) | Jacket T (° C.) |
| 300 | 1000 | 65 | 300 | 1500 | 63-65 | 100 | 1000 | 10 |

Once it has returned to ambient temperature, the grain obtained is discharged and calibrated by means of an Erweka AR402 drive unit equipped with an FGS-type oscillating calibrator on a 500 μm grid, at a speed of 10 cpm.

Step 2: Thermal Granulation by Means of Softisan 154 and Eudragit E PO

The grain obtained in step 1 is introduced into a high-shear granulator of Diosna P-VAC10 type in the proportions indicated in table 17. Depending on the density of the mixture, the total weight introduced is adjusted to the filling volume of the tank of the granulator so as to guarantee homogenization thereof throughout the thermal granulation process (ideally ⅔ of the volume).

TABLE 17

Centesimal formula of the grain

| | Ingredients | | % (w/w) |
|---|---|---|---|
| Grain Example 10 | Trazodone HCl | Active ingredient | 90.00 |
| | Softisan 154 | Hot-melt binder | |
| Eudragit E PO | | Thermoplastic polymer | 10.00 |
| Total | | | 100.0 |

The setpoint parameters used are indicated in table 18.

TABLE 18

| Mixing | | | Cooling | | |
|---|---|---|---|---|---|
| Paddle speed (rpm) | Lump breaker speed (rpm) | Jacket T (° C.) | Paddle speed (rpm) | Lump breaker speed (rpm) | Jacket T (° C.) |
| 300 | 800 | 53 | 100 | 800 | 10 |

Once it has returned to ambient temperature, the grain obtained is discharged and calibrated by means of an Erweka AR402 drive unit equipped with an FGS-type oscillating calibrator on a 500 μm grid, at a speed of 10 cpm.

Example 9

Compression of the Grain of Example 8, 60 mg Dosage

The grain produced according to example 8 is used in the production of tablets containing a 60 mg dose of trazodone hydrochloride. The mixing and then the lubrication are carried out according to the proportions indicated in table 19 by means of a cubic mixer equipped with a tank of suitable size or any other item of equipment ensuring good mixture homogeneity.

TABLE 19

| Orodispersible tablet centesimal composition | | | % (w/w) | Dosage 60 mg mg/tablet |
|---|---|---|---|---|
| Grain Example 11 | Trazodone HCl | Active ingredient | 20.00 | 60.00 |
| | Dynasan 114 | Hot-melt binder | 5.00 | 15.00 |
| | Eudragit E PO | Thermoplastic polymer | 2.94 | 8.93 |
| AcDisol | | Disintegrant | 2.00 | 6.00 |
| Crospovidone XL | | Disintegrant | 5.00 | 15.00 |
| Mannitol SD 200 | | Diluent | 60.26 | 180.77 |
| Flavoring | | Flavoring | 1.00 | 3.00 |
| Sucralose | | Sweetener | 1.00 | 3.00 |
| Syloid 244FP | | Humectant | 2.00 | 6.00 |
| Mg stearate | | Lubricant | 0.80 | 2.40 |
| Total | | | 100.0 | 300.0 |

The mixture is compressed on a Fette 102i rotary press equipped with a gravity distributor and 3 sets of matrix/convex round punches, diameter 10 mm, and a splitting bar. The target unit weight is 300 mg and the compression force is adjusted so as to obtain a target hardness of 25 N.

Example 10

Step 1: Thermal Granulation by Means of Lipoxol 3350+Trazodone

The active ingredient and the Lipoxol 3350 are introduced into a high-shear granulator of Diosna P-VAC10 type in the proportions indicated in table 20. Depending on the density of the mixture, the total weight introduced is adjusted by those skilled in the art to the filling volume of the tank of the granulator so as to guarantee homogenization thereof throughout the thermal granulation process (ideally ⅔ of the volume).

TABLE 20

Centesimal formula of the grain

| Ingredients | | % (w/w) | Weight (grams) |
|---|---|---|---|
| Trazodone HCl | Active ingredient | 80 | 480.00 |
| Lipoxol 3350 | Hot-melt binder | 20 | 120.00 |
| Total | | 100.0 | 600.00 |

The setpoint parameters used, namely: the paddle speed, the lump breaker speed and the setpoint temperature of the jacket, are indicated in table 21.

TABLE 21

| Mixing | | | Granulation | | | Cooling | | |
|---|---|---|---|---|---|---|---|---|
| Paddle speed (rpm) | Lump breaker speed (rpm) | Jacket T (° C.) | Paddle speed (rpm) | Lump breaker speed (rpm) | Jacket T (° C.) | Paddle speed (rpm) | Lump breaker speed (rpm) | Jacket T (° C.) |
| 300 | 1000 | 70 | 300 | 1500 | 65 | 100 | 1000 | 10 |

Once it has returned to ambient temperature, the grain obtained is discharged and calibrated by means of an Erweka AR402 drive unit equipped with an FGS-type oscillating calibrator on a 500 μm grid, at a speed of 10 cpm.

Step 2: Thermal Granulation by Means of Lipoxol 3350 and Eudragit E PO

The grain obtained in step 1 is introduced into a high-shear granulator of Diosna P-VAC10 type in the proportions indicated in table 22. Depending on the density of the mixture, the total weight introduced is adjusted to the filling volume of the tank of the granulator so as to guarantee homogenization thereof throughout the thermal granulation process (ideally ⅔ of the volume).

TABLE 22

Centesimal formula of the grain

| Ingredients | | | % (w/w) |
|---|---|---|---|
| Grain Example 13 | Trazodone HCl Lipoxol 3350 | Active ingredient Hot-melt binder | 90.00 |
| Eudragit E PO | | Thermoplastic polymer | 10.00 |
| Total | | | 100.0 |

The setpoint parameters used are indicated in table 23.

TABLE 23

| Mixing | | | Cooling | | |
|---|---|---|---|---|---|
| Paddle speed (rpm) | Lump breaker speed (rpm) | Jacket T (° C.) | Paddle speed (rpm) | Lump breaker speed (rpm) | Jacket T (° C.) |
| 200 | 800-700 | 53 | 100 | 700 | 10 |

Once it has returned to ambient temperature, the grain obtained is discharged and calibrated by means of an Erweka AR402 drive unit equipped with an FGS-type oscillating calibrator on a 500 μm grid, at a speed of 10 cpm.

Example 11

Compression of the Grain of Example 10, 60 mg Dosage

The grain produced according to example 10 is used in the production of tablets containing a 60 mg dose of trazodone hydrochloride. The mixing and then the lubrication are carried out according to the proportions indicated in table 24 by means of a cubic mixer equipped with a tank of suitable size or any other item of equipment ensuring good mixture homogeneity.

TABLE 24

| Orodispersible tablet centesimal composition | | | % (w/w) | Dosage 60 mg mg/tablet |
|---|---|---|---|---|
| Grain Example 14 | Trazodone HCl Lipoxol 3350 | Active ingredient Hot-melt binder | 20.00 5.00 | 60.00 15.00 |
| | Eudragit E PO | Thermoplastic polymer | 2.94 | 8.83 |
| AcDisol | | Disintegrant | 2.00 | 6.00 |
| Crospovidone XL | | Disintegrant | 5.00 | 15.00 |
| Mannitol SD 200 | | Diluent | 60.26 | 180.77 |
| Flavoring | | Flavoring | 1.00 | 3.00 |
| Sucralose | | Sweetener | 1.00 | 3.00 |
| Syloid 244FP | | Humectant | 2.00 | 6.00 |
| Mg stearate | | Lubricant | 0.80 | 2.40 |
| Total | | | 100.0 | 300.0 |

The mixture is compressed on a Fette 102i rotary press equipped with a gravity distributor and 3 sets of matrix/convex round punches, diameter 10 mm, and a splitting bar. The target unit weight is 300 mg and the compression force is adjusted so as to obtain a target hardness of 18 N.

Example 12

Step 1: Thermal Granulation by Means of Compritol HD5 ATO+Trazodone

The active ingredient and the Compritol HD5 ATO are introduced into a high-shear granulator of Diosna P-VAC10 type in the proportions indicated in table 25. Depending on the density of the mixture, the total weight introduced is adjusted by those skilled in the art to the filling volume of the tank of the granulator so as to guarantee homogenization thereof throughout the thermal granulation process (ideally ⅔ of the volume).

TABLE 25

Centesimal formula of the grain

| Ingredients | | % (w/w) | Weight (grams) |
|---|---|---|---|
| Trazodone HCl | Active ingredient | 80 | 480.00 |
| Compritol HD5 ATO | Hot-melt binder | 20 | 120.00 |
| Total | | 100.00 | 600.00 |

The setpoint parameters used, namely: the paddle speed, the lump breaker speed and the setpoint temperature of the jacket, are indicated in table 26.

TABLE 26

| Mixing | | | Granulation | | | Cooling | | |
|---|---|---|---|---|---|---|---|---|
| Paddle speed (rpm) | Lump breaker speed (rpm) | Jacket T (° C.) | Paddle speed (rpm) | Lump breaker speed (rpm) | Jacket T (° C.) | Paddle speed (rpm) | Lump breaker speed (rpm) | Jacket T (° C.) |
| 300 | 1000 | 70 | 300 | 1500 | 68-65 | 100 | 1000 | 10 |

Once it has returned to ambient temperature, the grain obtained is discharged and calibrated by means of an Erweka AR402 drive unit equipped with an FGS-type oscillating calibrator on a 500 µm grid, at a speed of 10 cpm.

Step 2: Thermal Granulation by Means of Compritol HD5 ATO and Eudragit E PO

The grain obtained in step 1 is introduced into a high-shear granulator of Diosna P-VAC10 type in the proportions indicated in table 27. Depending on the density of the mixture, the total weight introduced is adjusted to the filling volume of the tank of the granulator so as to guarantee homogenization thereof throughout the thermal granulation process (ideally ⅔ of the volume).

TABLE 27

Centesimal formula of the grain

| | Ingredients | | % (w/w) |
|---|---|---|---|
| Grain Example 16 | Trazodone HCl Compritol HD5 ATO | Active ingredient Hot-melt binder | 90.00 |
| Eudragit E PO | | Thermoplastic polymer | 10.00 |
| Total | | | 100.0 |

The setpoint parameters used are indicated in table 28.

TABLE 28

| Mixing | | | Cooling | | |
|---|---|---|---|---|---|
| Paddle speed (rpm) | Lump breaker speed (rpm) | Jacket T (° C.) | Paddle speed (rpm) | Lump breaker speed (rpm) | Jacket T (° C.) |
| 200-300 | 800 | 53 | 100 | 800 | 10 |

Once it has returned to ambient temperature, the grain obtained is discharged and calibrated by means of an Erweka AR402 drive unit equipped with an FGS-type oscillating calibrator on a 500 µm grid, at a speed of 10 cpm.

Example 13

Compression of the Grain of Example 12, 60 mg Dosage

The grain produced according to example 12 is used in the production of tablets containing a 60 mg dose of trazodone hydrochloride. The mixing and then the lubrication are carried out according to the proportions indicated in table 29 by means of a cubic mixer equipped with a tank of suitable size or any other item of equipment ensuring good mixture homogeneity.

TABLE 29

| Orodispersible tablet centesimal composition | | | % (w/w) | Dosage 60 mg mg/tablet |
|---|---|---|---|---|
| Grain Example 17 | Trazodone HCl Compritol HD5 ATO | Active ingredient Hot-melt binder | 20.00 5.00 | 60.00 15.00 |
| | Eudragit E PO | Thermoplastic polymer | 2.94 | 8.83 |
| AcDisol | | Disintegrant | 2.00 | 6.00 |
| Crospovidone XL | | Disintegrant | 5.00 | 15.00 |
| Mannitol SD 200 | | Diluent | 60.26 | 180.77 |
| Flavoring | | Flavoring | 1.00 | 3.00 |
| Sucralose | | Sweetener | 1.00 | 3.00 |
| Syloid 244FP | | Humectant | 2.00 | 6.00 |
| Mg stearate | | Lubricant | 0.80 | 2.40 |
| Total | | | 100.0 | 300.0 |

The mixture is compressed on a Fette 102i rotary press equipped with a gravity distributor and 3 sets of matrix/convex round punches, diameter 10 mm, and a splitting bar. The target unit weight is 300 mg and the compression force is adjusted so as to obtain a target hardness of 27 N.

Example 14

Step 1: Thermal Granulation by Means of Montane 60 PHA+Bitrex

A mixture of Bitrex and of 200M lactose representing the active ingredient and also the Montane 60 PHA are introduced into a high-shear granulator of Diosna P-VAC10 type in the proportions indicated in table 30. Depending on the density of the mixture, the total weight introduced is adjusted by those skilled in the art to the filling volume of the tank of the granulator so as to guarantee homogenization thereof throughout the thermal granulation process (ideally ⅔ of the volume).

TABLE 30

Centesimal formula of the grain

| Ingredients | | % (w/w) | Weight (grams) |
|---|---|---|---|
| Bitrex | Bitter agent | 80 | 0.25 |
| 200M lactose | Diluent | 79.95 | 399.75 |
| Montane 60PHA | Hot-melt binder | 20 | 100.00 |
| Total | | 100.00 | 500.00 |

The setpoint parameters used, namely: the paddle speed, the lump breaker speed and the setpoint temperature of the jacket, are indicated in table 31.

TABLE 31

| Mixing | | | Granulation | | | Cooling | | |
|---|---|---|---|---|---|---|---|---|
| Paddle speed (rpm) | Lump breaker speed (rpm) | Jacket T (° C.) | Paddle speed (rpm) | Lump breaker speed (rpm) | Jacket T (° C.) | Paddle speed (rpm) | Lump breaker speed (rpm) | Jacket T (° C.) |
| 300 | 1000 | 70 | 300 | 1500 | 60 | 100 | 1000-1500 | 10 |

Once it has returned to ambient temperature, the grain obtained is discharged and calibrated by means of an Erweka AR402 drive unit equipped with an FGS-type oscillating calibrator on a 500 μm grid, at a speed of 10 cpm.

Step 2: Thermal Granulation by Means of Montane 60 PHA and Eudragit E PO

The grain obtained in step 1 is introduced into a high-shear granulator of Diosna P-VAC10 type in the proportions indicated in table 32. Depending on the density of the mixture, the total weight introduced is adjusted to the filling volume of the tank of the granulator so as to guarantee homogenization thereof throughout the thermal granulation process (ideally ⅔ of the volume).

TABLE 32

Centesimal formula of the grain

| Ingredients | | | % (w/w) |
|---|---|---|---|
| Grain Example 19 | Bitrex | Bitter agent | 90.00 |
| | 200M lactose | Diluent | |
| | Montane 60PHA | Hot-melt binder | |
| Eudragit E PO | | Thermoplastic polymer | 10.00 |
| Total | | | 100.0 |

The setpoint parameters used are indicated in table 33.

TABLE 33

| Mixing | | | Cooling | | |
|---|---|---|---|---|---|
| Paddle speed (rpm) | Lump breaker speed (rpm) | Jacket T (° C.) | Paddle speed (rpm) | Lump breaker speed (rpm) | Jacket T (° C.) |
| 150 | 800 | 53 | 100 | 800 | 10 |

Once it has returned to ambient temperature, the grain obtained is discharged and calibrated by means of an Erweka AR402 drive unit equipped with an FGS-type oscillating calibrator on a 500 μm grid, at a speed of 10 cpm.

Example 15

Compression of the Grain of Example 14, 60 mg Dosage

The grain produced according to example 14 is used in the production of tablets containing a 60 mg dose of a mixture of 200M lactose and of Bitrex. The mixing and then the lubrication are carried out according to the proportions indicated in table 34 by means of a cubic mixer equipped with a tank of suitable size or any other item of equipment ensuring good mixture homogeneity.

TABLE 34

| Orodispersible tablet centesimal composition | | | % (w/w) | Dosage 60 mg mg/tablet |
|---|---|---|---|---|
| Ingredients | | | | |
| Grain Example 20 | Bitrex | Bitter agent | 0.0125 | 0.0375 |
| | 200M lactose | Diluent | 19.98 | 59.94 |
| | Montane 60PHA | Hot-melt binder | 5.00 | 14.99 |
| | Eudragit E PO | Thermoplastic polymer | 2.78 | 8.33 |
| AcDisol | | Disintegrant | 2.00 | 6.00 |
| Crospovidone XL | | Disintegrant | 5.00 | 15.00 |
| Mannitol SD 200 | | Diluent | 60.43 | 181.30 |
| Flavoring | | Flavoring | 1.00 | 3.00 |
| Sucralose | | Sweetener | 1.00 | 3.00 |
| Syloid 244FP | | Humectant | 2.00 | 6.00 |
| Mg stearate | | Lubricant | 0.80 | 2.40 |
| Total | | | 100.0 | 300.0 |

The mixture is compressed on a Fette 102i rotary press equipped with a gravity distributor and 3 sets of matrix/convex round punches, diameter 10 mm, and a splitting bar. The target unit weight is 300 mg and the compression force is adjusted so as to obtain a target hardness of 18 N.

Example 16

Step 1: Thermal Granulation by Means of Crodacol CS 50+Bitrex

A mixture of Bitrex and of 200M lactose representing the active ingredient and also the Crodacol CS 50 are introduced into a high-shear granulator of Diosna P-VAC10 type in the proportions indicated in table 35. Depending on the density of the mixture, the total weight introduced is adjusted by those skilled in the art to the filling volume of the tank of the granulator so as to guarantee homogenization thereof throughout the thermal granulation process (ideally ⅔ of the volume).

TABLE 35

Centesimal formula of the grain

| Ingredients | | % (w/w) | Weight (grams) |
|---|---|---|---|
| Bitrex | Bitter agent | 80 | 0.25 |
| 200M lactose | Diluent | 79.95 | 399.75 |
| Crodacol CS 50 | Hot-melt binder | 20 | 100.00 |
| Total | | 100.0 | 500.00 |

The setpoint parameters used, namely: the paddle speed, the lump breaker speed and the setpoint temperature of the jacket, are indicated in table 36.

TABLE 36

| Mixing | | | Granulation | | | Cooling | | |
|---|---|---|---|---|---|---|---|---|
| Paddle speed (rpm) | Lump breaker speed (rpm) | Jacket T (° C.) | Paddle speed (rpm) | Lump breaker speed (rpm) | Jacket T (° C.) | Paddle speed (rpm) | Lump breaker speed (rpm) | Jacket T (° C.) |
| 300 | 1000 | 70 | 300 | 1500 | 65 | 100-200 | 1000-1500 | 10 |

Once it has returned to ambient temperature, the grain obtained is discharged and calibrated by means of an Erweka AR402 drive unit equipped with an FGS-type oscillating calibrator on a 500 μm grid, at a speed of 10 cpm.

Step 2: Thermal Granulation by Means of Crodacol CS 50 and Eudragit E PO

The grain obtained in step 1 is introduced into a high-shear granulator of Diosna P-VAC10 type in the proportions indicated in table 37. Depending on the density of the mixture, the total weight introduced is adjusted to the filling volume of the tank of the granulator so as to guarantee homogenization thereof throughout the thermal granulation process (ideally ⅔ of the volume).

TABLE 37

Centesimal formula of the grain

| Ingredients | | | % (w/w) |
|---|---|---|---|
| Grain Example 22 | Bitrex | Bitter agent | 90.00 |
| | 200M lactose | Diluent | |
| | Crodacol CS 50 | Hot-melt binder | |
| Eudragit E PO | | Thermoplastic polymer | 10.00 |
| Total | | | 100.0 |

The setpoint parameters used are indicated in table 38.

TABLE 38

| Mixing | | | Cooling | | |
|---|---|---|---|---|---|
| Paddle speed (rpm) | Lump breaker speed (rpm) | Jacket T (° C.) | Paddle speed (rpm) | Lump breaker speed (rpm) | Jacket T (° C.) |
| 100 | 800 | 53 | 100 | 800 | 10 |

Once it has returned to ambient temperature, the grain obtained is discharged and calibrated by means of an Erweka AR402 drive unit equipped with an FGS-type oscillating calibrator on a 500 μm grid, at a speed of 10 cpm.

Example 17

Compression of the Grain of Example 16, 60 mg Dosage

The grain produced according to example 16 is used in the production of tablets containing a 60 mg dose of a mixture of 200M lactose and of Bitrex. The mixing and then the lubrication are carried out according to the proportions indicated in table 39 by means of a cubic mixer equipped with a tank of suitable size or any other item of equipment ensuring a good mixture homogeneity.

TABLE 39

| Orodispersible tablet centesimal composition | | | % (w/w) | Dosage 60 mg mg/tablet |
|---|---|---|---|---|
| Ingredients | | | | |
| Grain Example 23 | Bitrex | Bitter agent | 0.0125 | 0.0375 |
| | 200M lactose | Diluent | 19.98 | 59.94 |
| | Crodacol CS 50 | Hot-melt binder | 5.00 | 14.99 |
| | Eudragit E PO | Thermoplastic polymer | 2.78 | 8.33 |
| AcDisol | | Disintegrant | 2.00 | 6.00 |
| Crospovidone XL | | Disintegrant | 5.00 | 15.00 |
| Mannitol SD 200 | | Diluent | 60.43 | 181.30 |
| Flavoring | | Flavoring | 1.00 | 3.00 |
| Sucralose | | Sweetener | 1.00 | 3.00 |
| Syloid 244FP | | Humectant | 2.00 | 6.00 |
| Mg stearate | | Lubricant | 0.80 | 2.40 |
| Total | | | 100.0 | 300.0 |

The mixture is compressed on a Fette 102i rotary press equipped with a gravity distributor and 3 sets of matrix/convex round punches, diameter 10 mm, and a splitting bar. The target unit weight is 300 mg and the compression force is adjusted so as to obtain a target hardness of 19 N.

Example 18

Step 1: Thermal Granulation by Means of Crodacol S 95+Bitrex

A mixture of Bitrex and of 200M lactose representing the active ingredient and also the Crodacol S 95 are introduced into a high-shear granulator of Diosna P-VAC10 type in the proportions indicated in table 40. Depending on the density of the mixture, the total weight introduced is adjusted by those skilled in the art to the filling volume of the tank of the granulator so as to guarantee homogenization thereof throughout the thermal granulation process (ideally ⅔ of the volume).

TABLE 40

Centesimal formula of the grain

| Ingredients | | % (w/w) | Weight (grams) |
|---|---|---|---|
| Bitrex | Bitter agent | 80 | 0.25 |
| 200M lactose | Diluent | 79.95 | 399.75 |
| Crodacol S 95 | Hot-melt binder | 20 | 100.00 |
| Total | | 100.0 | 500.00 |

The setpoint parameters used, namely: the paddle speed, the lump breaker speed and the setpoint temperature of the jacket, are indicated in table 41.

TABLE 41

| Mixing | | | Granulation | | | Cooling | | |
|---|---|---|---|---|---|---|---|---|
| Paddle speed (rpm) | Lump breaker speed (rpm) | Jacket T (° C.) | Paddle speed (rpm) | Lump breaker speed (rpm) | Jacket T (° C.) | Paddle speed (rpm) | Lump breaker speed (rpm) | Jacket T (° C.) |
| 300 | 1000 | 70 | 300 | 1500 | 65 | 100 | 1000-1500 | 10 |

Once it has returned to ambient temperature, the grain obtained is discharged and calibrated by means of an Erweka AR402 drive unit equipped with an FGS-type oscillating calibrator on a 500 μm grid, at a speed of 10 cpm.

Step 2: Thermal Granulation by Means of Crodacol S 95 and Eudragit E PO

The grain in step 1 is introduced into a high-shear granulator of Diosna P-VAC10 type in the proportions indicated in table 42. Depending on the density of the mixture, the total weight introduced is adjusted to the filling volume of the tank of the granulator so as to guarantee homogenization thereof throughout the thermal granulation process (ideally ⅔ of the volume).

TABLE 42

Centesimal formula of the grain

| Ingredients | | | % (w/w) |
|---|---|---|---|
| Grain Example 25 | Bitrex | Bitter agent | 90.00 |
| | 200M lactose | Diluent | |
| | Crodacol S 95 | Hot-melt binder | |
| Eudragit E PO | | Thermoplastic polymer | 10.00 |
| Total | | | 100.0 |

The setpoint parameters used are indicated in table 43.

TABLE 43

| Mixing | | | Cooling | | |
|---|---|---|---|---|---|
| Paddle speed (rpm) | Lump breaker speed (rpm) | Jacket T (° C.) | Paddle speed (rpm) | Lump breaker speed (rpm) | Jacket T (° C.) |
| 150 | 800 | 55 | 100 | 800 | 10 |

Once it has returned to ambient temperature, the grain obtained is discharged and calibrated by means of an Erweka AR402 drive unit equipped with an FGS-type oscillating calibrator on a 500 μm grid, at a speed of 10 cpm.

Example 19

Compression of the Grain of Example 18, 60 mg Dosage

The grain produced according to example 18 is used in the production of tablets containing a 60 mg dose of a mixture of 200M lactose and of Bitrex. The mixing and then the lubrication are carried out according to the proportions indicated in table 44 by means of a cubic mixer equipped with a tank of suitable size or any other item of equipment ensuring a good mixture homogeneity.

TABLE 44

| Orodispersible tablet centesimal composition | | | | Dosage 60 mg |
|---|---|---|---|---|
| Ingredients | | | % (w/w) | mg/tablet |
| Grain Example 26 | Bitrex | Bitter agent | 0.0125 | 0.0375 |
| | 200M lactose | Diluent | 19.98 | 59.94 |
| | Crodacol S 95 | Hot-melt binder | 5.00 | 14.99 |
| | Eudragit E PO | Thermoplastic polymer | 2.78 | 8.33 |
| AcDisol | | Disintegrant | 2.00 | 6.00 |
| Crospovidone XL | | Disintegrant | 5.00 | 15.00 |
| Mannitol SD 200 | | Diluent | 60.43 | 181.30 |
| Flavoring | | Flavoring | 1.00 | 3.00 |
| Sucralose | | Sweetener | 1.00 | 3.00 |
| Syloid 244FP | | Humectant | 2.00 | 6.00 |
| Mg stearate | | Lubricant | 0.80 | 2.40 |
| Total | | | 100.0 | 300.0 |

The mixture is compressed on a Fette 102i rotary press equipped with a gravity distributor and 3 sets of matrix/convex round punches, diameter 10 mm, and a splitting bar. The target unit weight is 300 mg and the compression force is adjusted so as to obtain a target hardness of 16 N.

Example 20

Step 1: Thermal Granulation by Means of Crodacol C 95+Bitrex

A mixture of Bitrex and of 200M lactose representing the active ingredient and also the Crodacol C 95 are introduced into a high-shear granulator of Diosna P-VAC10 type in the proportions indicated in table 45. Depending on the density of the mixture, the total weight introduced is adjusted by those skilled in the art to the filling volume of the tank of the granulator so as to guarantee homogenization thereof throughout the thermal granulation process (ideally ⅔ of the volume).

TABLE 45

Centesimal formula of the grain

| Ingredients | | % (w/w) | Weight (grams) |
|---|---|---|---|
| Bitrex | Bitter agent | 80 | 0.25 |
| 200M lactose | Diluent | 79.95 | 399.75 |
| Crodacol S 95 | Hot-melt binder | 20 | 100.00 |
| Total | | 100.0 | 500.00 |

The setpoint parameters used, namely: the paddle speed, the lump breaker speed and the setpoint temperature of the jacket, are indicated in table 46.

TABLE 46

| Mixing | | | Granulation | | | Cooling | | |
|---|---|---|---|---|---|---|---|---|
| Paddle speed (rpm) | Lump breaker speed (rpm) | Jacket T (° C.) | Paddle speed (rpm) | Lump breaker speed (rpm) | Jacket T (° C.) | Paddle speed (rpm) | Lump breaker speed (rpm) | Jacket T (° C.) |
| 300 | 1000 | 65 | 300 | 1500 | 60 | 100 | 1000 | 10 |

Once it has returned to ambient temperature, the grain obtained is discharged and calibrated by means of an Erweka AR402 drive unit equipped with an FGS-type oscillating calibrator on a 500 μm grid, at a speed of 10 cpm.

Step 2: Thermal Granulation by Means of Crodacol C 95 and Eudragit E PO

The grain obtained in step 1 is introduced into a high-shear granulator of Diosna P-VAC10 type in the proportions indicated in table 47. Depending on the density of the mixture, the total weight introduced is adjusted to the filling volume of the tank of the granulator so as to guarantee homogenization thereof throughout the thermal granulation process (ideally ⅔ of the volume).

TABLE 47

Centesimal formula of the grain

| Ingredients | | | %(w/w) |
|---|---|---|---|
| Grain Example 28 | Bitrex 200M lactose Crodacol C 95 | Bitter agent Diluent Hot-melt binder | 90.00 |
| Eudragit E PO | | Thermoplastic polymer | 10.00 |
| Total | | | 100.0 |

The setpoint parameters used are indicated in table 48.

TABLE 48

| Mixing | | | Cooling | | |
|---|---|---|---|---|---|
| Paddle speed (rpm) | Lump breaker speed (rpm) | Jacket T (° C.) | Paddle speed (rpm) | Lump breaker speed (rpm) | Jacket T (° C.) |
| 200 | 800 | 53 | 100 | 800 | 10 |

Once it has returned to ambient temperature, the grain obtained is discharged and calibrated by means of an Erweka AR402 drive unit equipped with an FGS-type oscillating calibrator on a 500 μm grid, at a speed of 10 cpm.

Example 21

Compression of the Grain of Example 20, 60 mg Dosage

The grain produced according to example 20 is used in the production of tablets containing a 60 mg dose of a mixture of 200M lactose and of Bitrex. The mixing and then the lubrication are carried out according to the proportions indicated in table 49 by means of a cubic mixer equipped with a tank of suitable size or any other item of equipment ensuring a good mixture homogeneity.

TABLE 49

| Orodispersible tablet centesimal composition | | | | Dosage 60 mg |
|---|---|---|---|---|
| Ingredients | | | % (w/w) | mg/tablet |
| Grain Example 29 | Bitrex 200M lactose Crodacol C 95 Eudragit E PO | Bitter agent Diluent Hot-melt binder Thermoplastic polymer | 0.0125 19.98 5.00 2.78 | 0.0375 59.94 14.99 8.33 |

TABLE 49-continued

| Orodispersible tablet centesimal composition | | | Dosage 60 mg |
|---|---|---|---|
| Ingredients | | % (w/w) | mg/tablet |
| AcDisol | Disintegrant | 2.00 | 6.00 |
| Crospovidone XL | Disintegrant | 5.00 | 15.00 |
| Mannitol SD 200 | Diluent | 60.43 | 181.30 |
| Flavoring | Flavoring | 1.00 | 3.00 |
| Sucralose | Sweetener | 1.00 | 3.00 |
| Syloid 244FP | Humectant | 2.00 | 6.00 |
| Mg stearate | Lubricant | 0.80 | 2.40 |
| Total | | 100.0 | 300.0 |

The mixture is compressed on a Fette 102i rotary press equipped with a gravity distributor and 3 sets of matrix/convex round punches, diameter 10 mm, and a splitting bar. The target unit weight is 300 mg and the compression force is adjusted so as to obtain a target hardness of 14 N.

Example 22

Compression of the Active Ingredient without Taste Masking

The active ingredient is used in the production of tablets containing a 30 mg dose of trazodone hydrochloride. The mixing and then the lubrication are carried out according to the proportions indicated in table 50 by means of a cubic mixer equipped with a tank of suitable size or any other item of equipment ensuring good mixture homogeneity.

TABLE 50

| Centesimal formula | | | Dosage 30 mg |
|---|---|---|---|
| Ingredients | | % (w/w) | mg/tablet |
| Trazodone HCl API | Active ingredient | 15.00 | 30.00 |
| AcDisol | Disintegrant | 5.00 | 10.00 |
| Polyplasdone XL | Disintegrant | 2.00 | 4.00 |
| Mannitol SD 200 | Diluent | 72.20 | 144.40 |
| Flavoring | Flavoring | 1.00 | 2.00 |
| Sucralose | Sweetener | 1.00 | 2.00 |
| Dye | Dye | 1.00 | 2.00 |
| Syloid 244FP | Humectant | 2.00 | 4.00 |
| Mg stearate | Lubricant | 0.80 | 1.60 |
| Total | | 100.0 | 200.0 |

The mixture is compressed on a Fette 102i rotary press equipped with a gravity distributor and 3 sets of matrix/round punches, diameter 8 mm, and 1 splitting bar. The target unit weight is 200 mg and the compression force is adjusted so as to obtain a target hardness of 60 N.

Example 23

Physical Characterization of the Tablets

Measurement of the Weight of the Tablets

The weight of the tablets is measured on a Mettler Toledo AG245 balance (precision 0.1/0.01 mg) on a representative sample of 10 tablets.

Measurement of the Hardness

The hardness is measured according to the method described in European Pharmacopeia 8.0 (chapter 2.9.8. "Resistance to crushing of tablets").

Measurement of the Friability

The friability is measured according to the method described in European Pharmacopeia 8.0 (chapter 2.9.7. "Friability of uncoated tablets").

Measurement of the Disintegration Time

The disintegration time is measured according to the method described in European Pharmacopeia 8.0 (chapter 2.9.1. "Friability of uncoated tablets").

TABLE 51

| | Example 3 | Example 4 | Example 5 | Example 7 |
|---|---|---|---|---|
| Target dosage | 30 mg | 30 mg | 90 mg | 60 mg |
| Compression force | 4.4 kN | 2.6 kN | 4.2 kN | 5.2 kN |
| Hardness | 63 ± 2N | 32 ± 1N | 31 ± 0.7N | 22 ± 0.6N |
| Disintegration time | 35 seconds | 12 seconds | 19 seconds | 25 seconds |

| | Example 9 | Example 11 | Example 13 | Example 15 |
|---|---|---|---|---|
| Target dosage | 60 mg | 60 mg | 60 mg | 60 mg |
| Compression force | 5.5 kN | 4.8 kN | 5 kN | 4.3 kN |
| Hardness | 25 ± 0.5N | 18 ± 0.5N | 27 ± 0.1N | 18 ± 0.1N |
| Disintegration time | 25 seconds | 24 seconds | 21 seconds | 32 seconds |

| | Example 17 | Example 19 | Example 21 | Example 22 |
|---|---|---|---|---|
| Target dosage | 60 mg | 60 mg | 60 mg | 30 mg |
| Compression force | 5.5 kN | 4.8 kN | 5.8 kN | 5.2 kN |
| Hardness | 19 ± 0.6N | 16 ± 0.8N | 14 ± 0.5N | 60 ± 3N |
| Disintegration time | 31 seconds | 23 seconds | 24 seconds | 17 seconds |

Example 24

Measurement of the Dissolution of the Active Ingredient

The dissolution of the trazodone hydrochloride is measured with continuous stirring after introduction of the tablets into a dissolution apparatus of type 2 described in European Pharmacopeia 8.0 (chapter 2.9.3. "Dissolution test for solid dosage forms") equipped with paddles (stirring speed 50 rpm). The dissolution medium used consists of 500 ml of 0.01 N HCl and is maintained at a constant temperature of 37° C. (±0.5° C.) The continuous dosage of the active ingredient is measured by UV detection at λ=311 nm (10 mm cuvettes).

Figure 1:
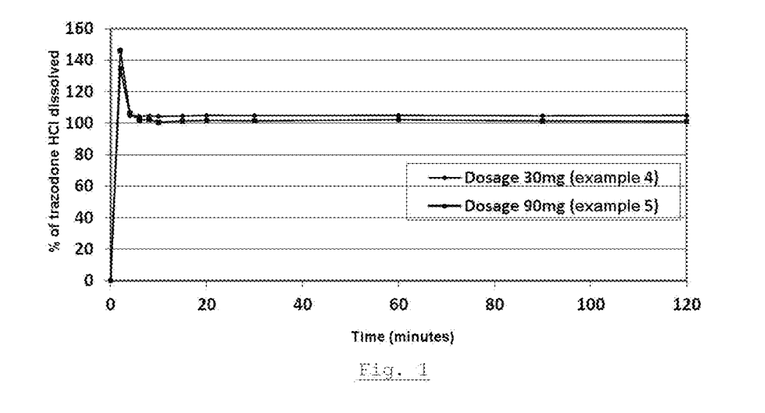
FIG. 1 represents the dissolution profile of the orodispersible tablets according to the invention produced according to examples 4 and 5.

The results obtained for the tablets produced according to examples 5 and 6 are reported in FIG. 1.

Example 25

Measuring of the Taste Masking by Electronic Tongue

The taste masking is measured using an Astree electronic tongue equipped with set #2 for pharmaceutical applications, composed of 7 sensory sensors (ZZ, AB, GA, BB, CA, DA, JE).

Each tablet is dissolved in deionized water (2 tablets in 50 ml). After complete disintegration with magnetic stirring, the suspensions are filtered through paper (porosity of 10 to 20 µm). The filtered solutions are poured into 25 ml beakers and placed on a 48-position carousel autosampler for immediate analysis.

The analysis conditions are the following:
Sample volume of 25 ml,
Acquisition time of 120 seconds,
Analysis time of 180 seconds.

The signal measured by the electronic tongue is measured at equilibrium (obtained in 100 to 120 seconds on average) on the 7 sensors. The measurement is taken three times for each sample and the sensors are rinsed with deionized water between each measurement.

These measurements are carried out on the tablets of examples 3, 4 and 22.

Placebo tablets are prepared in the same way as the tablets of examples 3, 4 and 22, but without active ingredient. The measurement by electronic tongue is also carried out three times using these placebo tablets.

Figure 2:
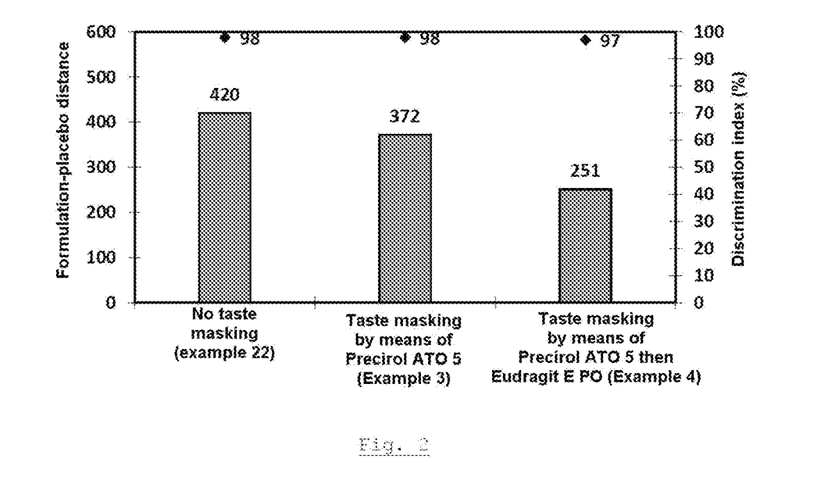
FIG. 2 represents the distances obtained with an electronic tongue for the tablets produced according to examples 3, 4 and 22.
Figure 3:
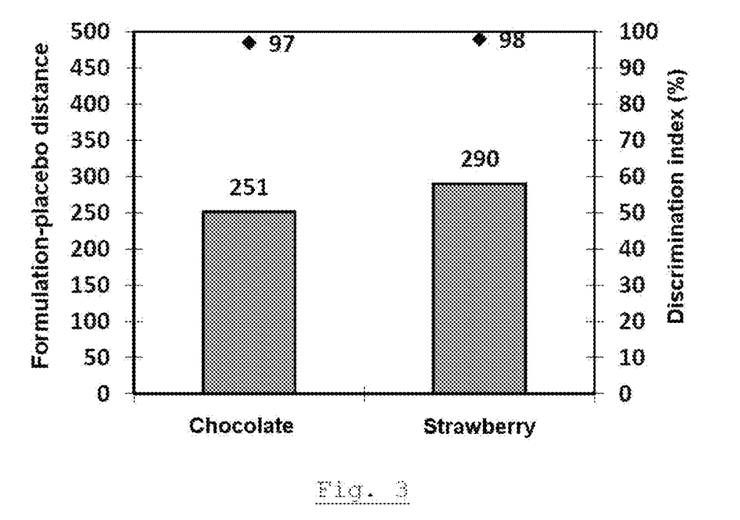
FIG. 3 represents the distances obtained with an electronic tongue for the tablets produced according to example 5, with a chocolate flavoring and a strawberry flavoring.

The data generated are processed by multidimensional statistical analysis using the AlphaSoft software in its version V14.1. For each tablet-placebo pair, the software calculates the Euclidean distance between the values obtained with the formulation containing the active ingredient and the values obtained with the corresponding placebo. The lower this value, the more efficient the masking of the taste of trazodone HCl. The results obtained for examples 3, 4 and 22 are reported in FIGS. 2 and 3.

The invention claimed is:

1. A method for producing granules of active ingredient with double taste masking, the method comprising performing (a) and (b) as two successive steps:
   (a) thermally granulating an active ingredient with a first compound to form first granules at at least a melting temperature of the first compound; and then
   (b) thermally granulating the first granules with a second compound at a temperature below (a) and at at least the glass thermoplastic temperature of the second compound to form granules of the active ingredient with double taste masking provided by the combination of the first compound and the second compound,
   wherein:
   the first compound comprises a hot-melt compound selected from waxes, hydrogenated vegetable oils, fatty acids, monoesters of fatty acids, diesters of fatty acids, triesters of fatty acids, monoesters of glycerol, diesters of glycerol, triesters of glycerol, triglycerides, glycerides, polyoxylglycerides, fatty acids, or mixtures of any of the foregoing hot-melt compounds and the second compound comprises a thermoplastic polymer that is soluble at a gastric pH less than or equal to 5, wherein the thermoplastic polymer is a cationic copolymer based on alkyl methacrylate and alkylamine methacrylate;
   and
   each thermal granulation step (a) and (b) is divided into three phases, the three phases comprising:
   mixing at constant paddle and lump breaker speeds while increasing temperature;
   granulating at stable temperature while increasing paddle and lump breaker speeds relative to the mixing step; and
   cooling by decreasing temperature while decreasing paddle and lump breaker speeds relative to the granulating step.

2. The method of claim 1, wherein:
   the first compound is chosen from the hot-melt compounds (i); and
   the second compound is chosen from the thermoplastic polymers (ii).

3. The method of claim 2, wherein the active ingredient is trazodone.

4. The method of claim 2, wherein:
the active ingredient is trazodone;
the first compound is glyceryl distearate; and
the second compound is a cationic copolymer of dimethylaminoethyl methacrylate, butyl methacrylate, and methyl methacrylate.

5. The method of claim 1, wherein the granules of active ingredient with double taste masking are free of any trace of solvent.

6. The method of claim 1, wherein the granules of active ingredient with double taste masking consist of the active ingredient, the first compound, and the second compound.

7. The method of claim 1, wherein each thermal granulation step (a) and (b) is carried out in a high-shear granulator.

8. The method of claim 1, wherein:
the first granules consist of the active ingredient and the first compound; and
the granules of active ingredient with double taste masking consist of the active ingredient, the first compound, and the second compound.

9. The method of claim 8, wherein:
the active ingredient is trazodone;
the first compound is glyceryl distearate; and
the second compound is a cationic copolymer of dimethylaminoethyl methacrylate, butyl methacrylate, and methyl methacrylate.

10. The method of claim 1, wherein:
each thermal granulation step (a) and (b) is carried out in a high-shear granulator in the absence of solvent;
the first granules consist of the active ingredient and the first compound; and
the granules of active ingredient with double taste masking consist of the active ingredient, the first compound, and the second compound.

11. The method of claim 10, wherein:
the active ingredient is trazodone;
the first compound is glyceryl distearate; and
the second compound is a cationic copolymer of dimethylaminoethyl methacrylate, butyl methacrylate, and methyl methacrylate.

12. The method of claim 1, further comprising returning the first granules to ambient temperature and discharging prior to (b).

13. The method of claim 1, further comprising calibrating the first granules to 500 µm prior to (b).

14. The method of claim 13, further comprising calibrating the first granules to 500 µm after (b).

15. The method of claim 1, wherein the granules with double taste masking are of 70-85% by weight the active ingredient, 8 to 20% by weight the hot-melt compound and 10 to 20% by weight the thermoplastic polymer.

* * * * *